(12) United States Patent
Druilhe

(10) Patent No.: US 7,488,489 B2
(45) Date of Patent: Feb. 10, 2009

(54) **IDENTIFICATION OF A CONSERVED REGION OF *PLASMODIUM FALCIPARUM* MSP3 TARGETED BY BIOLOGICALLY ACTIVE ANTIBODIES**

(75) Inventor: Pierre Druilhe, Paris (FR)

(73) Assignee: Institut Pasteur, Paris (FR)

( * ) Notice: Subject to any disclaimer, the term of this patent is extended or adjusted under 35 U.S.C. 154(b) by 432 days.

(21) Appl. No.: 11/189,817

(22) Filed: Jul. 27, 2005

(65) Prior Publication Data

US 2006/0030006 A1 Feb. 9, 2006

Related U.S. Application Data

(60) Provisional application No. 60/598,062, filed on Aug. 3, 2004.

(51) Int. Cl.
*A61K 39/015* (2006.01)
(52) U.S. Cl. .............. 424/268.1; 530/300; 530/350; 424/269.1; 424/192.1; 424/193.1; 424/191.1; 424/272.1
(58) Field of Classification Search .............. 530/300, 530/350; 424/269.1, 192.1, 193.1, 191.1, 424/268.1, 272.1
See application file for complete search history.

(56) References Cited

U.S. PATENT DOCUMENTS 6,017,538 A * 1/2000 Druilhe et al. ............ 424/191.1
2005/0112133 A1* 5/2005 Druilhe .................... 424/185.1

FOREIGN PATENT DOCUMENTS

WO 94/09140 * 4/1994
WO 2004/043488 * 5/2004

OTHER PUBLICATIONS

Gardner et al (Nature 419:498-511. 2002).*
McColl et al (Mol.Biochem.Parasitol. 1997. 90: 21-31).*
Okenu et al (Mol. Biochem. Parasitol. 109:185-188(2000)).*
Huber et al (Mol. Biochem. Parasitol. 87:231-234(1997).*
Eisen et al (Submitted 1999; EMBL AF213689).*
Hisaeda et al (J. Infect. Dis. 185:657-664. 2002. "Merozoite surface protein 3 and protection against malaria in *Aotus nancymai* monkeys").*

* cited by examiner

*Primary Examiner*—Jennifer E Graser
(74) *Attorney, Agent, or Firm*—Oblon, Spivak, McClelland, Maier & Neustadt, P.C.

(57) ABSTRACT

Antigenic and immunogenic determinants of Merozoite surface protein 3 (MSP3). Antigenicity and functional assays identified a 68-amino acid conserved domain of MSP3 as a target of biologically active antibodies. A peptide comprising amino acid residues 184-251 of SEQ ID NO: 2, may also be employed as may peptides consisting of different combinations of the MSP3 a, b, c, d, e and f peptides. Particular non-overlapping or overlapping segments of MSP3 a, b, c, d, e and f peptides may also be used. The various overlapping segments and nonoverlapping segments among the different MSP3 peptides are shown in FIG. 6. MSP3 determinants include targets of antibody-dependent cellular inhibition (ADCI) which is a protective mechanism against *Plasmodium falciparum* malaria. Six overlapping peptides were derived from the C-terminal end of the MSP3 polypeptide. Each of these peptides defined at least 1 non-crossreactive B cell epitope and contained T helper epitopes. Distinct patterns of antibody responses, by level and IgG subclass distribution, were observed to MSP3 peptides in inhabitants of a malaria-endemic area. Antibodies affinity purified toward each peptide differed in their functional capacity to mediate parasite killing in ADCI assays: 3 of 6 overlapping peptides had a major inhibitory effect on parasite growth. Passive transfer of anti-MSP3 antibodies in vivo in a *P. falciparum* mouse model confirmed the functional properties of antibodies to these MSP3 determinants.

29 Claims, 6 Drawing Sheets

Fig. 6

MSP-3 protein
NP_700818          354 (3D7)

```
         1         10        20        30        40
         MKSFINITLSLFLLHLYIYINNVASKEIVKKYNLNLRNAILNNN 50        60        70        80        90       100
SQIENEENVNTTITGNDFSGGEFLWPGYTEELKAKKASEDAEKAANDAENASKEAEEA 110       120       130       140       150       160
AKEAVNLKESDKSYTKAKEACTAASKAKKAVETALKAKDDAEKSSKADSISTKTKEYA 170       180       190       200       210
EKAKNAYEKAKNAYQKANQAVLKAKEASSYDYILGWEFGGGVPEHKKEENMLSHLYVS 220       230       240       250       260       270
SKDKENISKENDDVLDEKEEEAEETEEEELEEKNEEETESEISEDEEEEEEEEKEEE 280       290       300       310       320       330
NDKKKEQEKEQSNENNDQKKDMEAQNLISKNQNNNEKNVKEAAESIMKTLAGLIKGNN 340       350
QIDSTLKDLVEELSKYFKNH
```

| | | |
|---|---|---|
| MSP3a<br>Oeuvray<br>(1994) | YEKAKNAYQKANQAVLKAKEASSYD (167-191)<br>HERAKNAYQKANQAVLKAKEASSY | |
| MSP3b<br>Oeuvray<br>(1994) | AKEASSYDYILGWEFGGGVPEHKKEEN (184-210)<br>AKEASSYDYILGWEFGGGVPEHKKEEN (pas nouveau) | 27AA |
| MSP3c<br>Oeuvray<br>(1994) | PEHKKEENMLSHLYVSSKDKENISKEND (203-230)<br>PEHKKEENMLSHLYVSSKDKENISKENE | 28AA |
| MSP3d | MLSHLYVSSKDKENISKENDDVLDEKEEEAEETEEEELEEK (211-251) | 41 AA |
| MSP3e | ENDKKKEQEKEQSNENNDQKKDMEAQNLISKN (276-307) | |
| MSP3f | NLISKNQNNNEKNVKEAAESIMKTLAGLIKGNNQIDSTLKDLVEELSKYFKNH (302-354) | |

Overlapping peptide : MSP3b+MSP3c+MSP3d

Positions 184 to 251 :  68 residus
AKEASSYDYILGWEFGGGVPEHKKEENMLSHLYVSSKDKENISKENDDVLDEKEEEAEETEEEELEEK

SEQUENCE LISTING

<160> NUMBER OF SEQ ID NOS: 14

<210> SEQ ID NO 1
<211> LENGTH: 1065
<212> TYPE: DNA
<213> ORGANISM: Plasmodium falciparum
<220> FEATURE:
<221> NAME/KEY: CDS
<222> LOCATION: (1)..(1065)
<223> OTHER INFORMATION: MSP3 coding sequence

<400> SEQUENCE: 1

| | | | | | | | | | | | | | | | | |
|---|---|---|---|---|---|---|---|---|---|---|---|---|---|---|---|---|
| atg | aaa | agt | ttt | ata | aat | att | act | ctt | tca | tta | ttt | ttg | tta | cat | tta | 48 |
| Met | Lys | Ser | Phe | Ile | Asn | Ile | Thr | Leu | Ser | Leu | Phe | Leu | Leu | His | Leu | |
| 1 | | | | 5 | | | | | 10 | | | | | 15 | | |

| tat | att | tat | ata | aat | aat | gtt | gct | agt | aaa | gaa | att | gta | aaa | aaa | tat | 96 |
|---|---|---|---|---|---|---|---|---|---|---|---|---|---|---|---|---|
| Tyr | Ile | Tyr | Ile | Asn | Asn | Val | Ala | Ser | Lys | Glu | Ile | Val | Lys | Lys | Tyr | |
| | | | 20 | | | | | 25 | | | | | 30 | | | |

| aat | ctt | aac | tta | aga | aat | gca | ata | ttg | aat | aat | aat | tct | caa | ata | gaa | 144 |
|---|---|---|---|---|---|---|---|---|---|---|---|---|---|---|---|---|
| Asn | Leu | Asn | Leu | Arg | Asn | Ala | Ile | Leu | Asn | Asn | Asn | Ser | Gln | Ile | Glu | |
| | | | 35 | | | | | 40 | | | | | 45 | | | |

| aat | gaa | gaa | aat | gta | aat | act | aca | att | act | ggt | aat | gat | ttt | agt | ggt | 192 |
|---|---|---|---|---|---|---|---|---|---|---|---|---|---|---|---|---|
| Asn | Glu | Glu | Asn | Val | Asn | Thr | Thr | Ile | Thr | Gly | Asn | Asp | Phe | Ser | Gly | |
| 50 | | | | | 55 | | | | | 60 | | | | | | |

| gga | gaa | ttt | ttg | tgg | cct | ggt | tat | acg | gaa | gaa | tta | aaa | gct | aaa | aaa | 240 |
|---|---|---|---|---|---|---|---|---|---|---|---|---|---|---|---|---|
| Gly | Glu | Phe | Leu | Trp | Pro | Gly | Tyr | Thr | Glu | Glu | Leu | Lys | Ala | Lys | Lys | |
| 65 | | | | 70 | | | | | 75 | | | | | 80 | | |

| gct | tcc | gaa | gat | gct | gaa | aaa | gct | gct | aat | gat | gct | gaa | aat | gct | tca | 288 |
|---|---|---|---|---|---|---|---|---|---|---|---|---|---|---|---|---|
| Ala | Ser | Glu | Asp | Ala | Glu | Lys | Ala | Ala | Asn | Asp | Ala | Glu | Asn | Ala | Ser | |
| | | | | 85 | | | | | 90 | | | | | 95 | | |

| aaa | gag | gca | gaa | gaa | gct | gct | aaa | gaa | gca | gta | aat | tta | aag | gaa | tct | 336 |
|---|---|---|---|---|---|---|---|---|---|---|---|---|---|---|---|---|
| Lys | Glu | Ala | Glu | Glu | Ala | Ala | Lys | Glu | Ala | Val | Asn | Leu | Lys | Glu | Ser | |
| | | | 100 | | | | | 105 | | | | | 110 | | | |

| gat | aaa | tct | tat | aca | aaa | gca | aaa | gaa | gca | tgt | aca | gct | gct | tca | aag | 384 |
|---|---|---|---|---|---|---|---|---|---|---|---|---|---|---|---|---|
| Asp | Lys | Ser | Tyr | Thr | Lys | Ala | Lys | Glu | Ala | Cys | Thr | Ala | Ala | Ser | Lys | |
| | | | 115 | | | | | 120 | | | | | 125 | | | |

| gca | aag | aaa | gct | gtt | gaa | act | gct | tta | aag | gca | aaa | gat | gat | gct | gaa | 432 |
|---|---|---|---|---|---|---|---|---|---|---|---|---|---|---|---|---|
| Ala | Lys | Lys | Ala | Val | Glu | Thr | Ala | Leu | Lys | Ala | Lys | Asp | Asp | Ala | Glu | |
| | | 130 | | | | | 135 | | | | | 140 | | | | |

| aaa | tct | tca | aaa | gct | gat | agt | att | tct | aca | aaa | aca | aaa | gaa | tat | gct | 480 |
|---|---|---|---|---|---|---|---|---|---|---|---|---|---|---|---|---|
| Lys | Ser | Ser | Lys | Ala | Asp | Ser | Ile | Ser | Thr | Lys | Thr | Lys | Glu | Tyr | Ala | |
| 145 | | | | | 150 | | | | | 155 | | | | | 160 | |

| gaa | aaa | gca | aaa | aat | gct | tat | gaa | aag | gca | aaa | aat | gct | tat | caa | aaa | 528 |
|---|---|---|---|---|---|---|---|---|---|---|---|---|---|---|---|---|
| Glu | Lys | Ala | Lys | Asn | Ala | Tyr | Glu | Lys | Ala | Lys | Asn | Ala | Tyr | Gln | Lys | |
| | | | | 165 | | | | | 170 | | | | | 175 | | |

| gca | aac | caa | gct | gtt | tta | aaa | gca | aaa | gaa | gct | tct | agt | tat | gat | tat | 576 |
|---|---|---|---|---|---|---|---|---|---|---|---|---|---|---|---|---|
| Ala | Asn | Gln | Ala | Val | Leu | Lys | Ala | Lys | Glu | Ala | Ser | Ser | Tyr | Asp | Tyr | |
| | | | 180 | | | | | 185 | | | | | 190 | | | |

| att | tta | ggt | tgg | gaa | ttt | gga | gga | ggc | gtt | cca | gaa | cac | aaa | aaa | gaa | 624 |
|---|---|---|---|---|---|---|---|---|---|---|---|---|---|---|---|---|
| Ile | Leu | Gly | Trp | Glu | Phe | Gly | Gly | Gly | Val | Pro | Glu | His | Lys | Lys | Glu | |
| | | | 195 | | | | | 200 | | | | | 205 | | | |

| gaa | aat | atg | tta | tca | cat | tta | tat | gtt | tct | tca | aag | gat | aag | gaa | aat | 672 |
|---|---|---|---|---|---|---|---|---|---|---|---|---|---|---|---|---|
| Glu | Asn | Met | Leu | Ser | His | Leu | Tyr | Val | Ser | Ser | Lys | Asp | Lys | Glu | Asn | |
| | | 210 | | | | | 215 | | | | | 220 | | | | |

| ata | tct | aag | gaa | aat | gat | gat | gta | tta | gat | gag | aag | gaa | gaa | gag | gca | 720 |
|---|---|---|---|---|---|---|---|---|---|---|---|---|---|---|---|---|
| Ile | Ser | Lys | Glu | Asn | Asp | Asp | Val | Leu | Asp | Glu | Lys | Glu | Glu | Glu | Ala | |
| 225 | | | | | 230 | | | | | 235 | | | | | 240 | |

| gaa | gaa | aca | gaa | gaa | gaa | gaa | ctt | gaa | gaa | aaa | aat | gaa | gaa | gaa | aca | 768 |
|---|---|---|---|---|---|---|---|---|---|---|---|---|---|---|---|---|
| Glu | Glu | Thr | Glu | Glu | Glu | Glu | Leu | Glu | Glu | Lys | Asn | Glu | Glu | Glu | Thr | |
| | | | | 245 | | | | | 250 | | | | | 255 | | |

```
gaa tca gaa ata agt gaa gat gaa gaa gaa gaa gaa gaa gaa         816
Glu Ser Glu Ile Ser Glu Asp Glu Glu Glu Glu Glu Glu Glu
        260             265             270 aag gaa gaa gaa aat gac aaa aaa gaa caa gaa aaa gaa caa agt     864
Lys Glu Glu Glu Asn Asp Lys Lys Glu Gln Glu Lys Glu Gln Ser
            275             280             285 aat gaa aat aat gat caa aaa aaa gat atg gaa gca cag aat tta att 912
Asn Glu Asn Asn Asp Gln Lys Lys Asp Met Glu Ala Gln Asn Leu Ile
290             295             300 tct aaa aac cag aat aat aat gag aaa aac gta aaa gaa gct gct gaa 960
Ser Lys Asn Gln Asn Asn Asn Glu Lys Asn Val Lys Glu Ala Ala Glu
305             310             315             320 agc atc atg aaa act tta gct ggt tta atc aag gga aat aat caa ata 1008
Ser Ile Met Lys Thr Leu Ala Gly Leu Ile Lys Gly Asn Asn Gln Ile
            325             330             335 gat tct acc tta aaa gat tta gta gaa gaa tta tcc aaa tat ttt aaa 1056
Asp Ser Thr Leu Lys Asp Leu Val Glu Glu Leu Ser Lys Tyr Phe Lys
            340             345             350 aat cat taa                                                     1065
Asn His
```

<210> SEQ ID NO 2
<211> LENGTH: 354
<212> TYPE: PRT
<213> ORGANISM: Plasmodium falciparum

<400> SEQUENCE: 2

```
Met Lys Ser Phe Ile Asn Ile Thr Leu Ser Leu Phe Leu Leu His Leu
1               5                   10                  15

Tyr Ile Tyr Ile Asn Asn Val Ala Ser Lys Glu Ile Val Lys Lys Tyr
            20                  25                  30

Asn Leu Asn Leu Arg Asn Ala Ile Leu Asn Asn Asn Ser Gln Ile Glu
        35                  40                  45

Asn Glu Glu Asn Val Asn Thr Thr Ile Thr Gly Asn Asp Phe Ser Gly
    50                  55                  60

Gly Glu Phe Leu Trp Pro Gly Tyr Thr Glu Leu Lys Ala Lys Lys
65                  70                  75                  80

Ala Ser Glu Asp Ala Glu Lys Ala Ala Asn Asp Ala Glu Asn Ala Ser
                85                  90                  95

Lys Glu Ala Glu Glu Ala Ala Lys Glu Ala Val Asn Leu Lys Glu Ser
            100                 105                 110

Asp Lys Ser Tyr Thr Lys Ala Lys Glu Ala Cys Thr Ala Ala Ser Lys
        115                 120                 125

Ala Lys Lys Ala Val Glu Thr Ala Leu Lys Ala Lys Asp Asp Ala Glu
    130                 135                 140

Lys Ser Ser Lys Ala Asp Ser Ile Ser Thr Lys Thr Lys Glu Tyr Ala
145                 150                 155                 160

Glu Lys Ala Lys Asn Ala Tyr Glu Lys Ala Lys Asn Ala Tyr Gln Lys
                165                 170                 175

Ala Asn Gln Ala Val Leu Lys Ala Glu Ala Ser Ser Tyr Asp Tyr
            180                 185                 190

Ile Leu Gly Trp Glu Phe Gly Gly Val Pro Glu His Lys Lys Glu
        195                 200                 205

Glu Asn Met Leu Ser His Leu Tyr Val Ser Ser Lys Asp Lys Glu Asn
    210                 215                 220

Ile Ser Lys Glu Asn Asp Asp Val Leu Asp Glu Lys Glu Glu Glu Ala
```

```
                    225                 230                 235                 240

Glu Glu Thr Glu Glu Glu Leu Glu Glu Lys Asn Glu Glu Thr
                    245                 250                 255

Glu Ser Glu Ile Ser Glu Asp Glu Glu Glu Glu Glu Glu Glu
                260                 265                 270

Lys Glu Glu Glu Asn Asp Lys Lys Glu Gln Glu Lys Glu Gln Ser
            275                 280                 285

Asn Glu Asn Asn Asp Gln Lys Lys Asp Met Glu Ala Gln Asn Leu Ile
        290                 295                 300

Ser Lys Asn Gln Asn Asn Glu Lys Asn Val Lys Glu Ala Ala Glu
305                 310                 315                 320

Ser Ile Met Lys Thr Leu Ala Gly Leu Ile Lys Gly Asn Asn Gln Ile
                325                 330                 335

Asp Ser Thr Leu Lys Asp Leu Val Glu Glu Leu Ser Lys Tyr Phe Lys
            340                 345                 350

Asn His

<210> SEQ ID NO 3
<211> LENGTH: 75
<212> TYPE: DNA
<213> ORGANISM: Plasmodium falciparum
<220> FEATURE:
<221> NAME/KEY: CDS
<222> LOCATION: (1)..(75)
<223> OTHER INFORMATION: MSP3a coding sequence

<400> SEQUENCE: 3 tat gaa aag gca aaa aat gct tat caa aaa gca aac caa gct gtt tta       48
Tyr Glu Lys Ala Lys Asn Ala Tyr Gln Lys Ala Asn Gln Ala Val Leu
1               5                   10                  15 aaa gca aaa gaa gct tct agt tat gat                                   75
Lys Ala Lys Glu Ala Ser Ser Tyr Asp
            20                  25

<210> SEQ ID NO 4
<211> LENGTH: 25
<212> TYPE: PRT
<213> ORGANISM: Plasmodium falciparum

<400> SEQUENCE: 4

Tyr Glu Lys Ala Lys Asn Ala Tyr Gln Lys Ala Asn Gln Ala Val Leu
1               5                   10                  15

Lys Ala Lys Glu Ala Ser Ser Tyr Asp
            20                  25

<210> SEQ ID NO 5
<211> LENGTH: 81
<212> TYPE: DNA
<213> ORGANISM: Plasmodium falciparum
<220> FEATURE:
<221> NAME/KEY: CDS
<222> LOCATION: (1)..(81)
<223> OTHER INFORMATION: MSP3b coding sequence

<400> SEQUENCE: 5 gca aaa gaa gct tct agt tat gat tat att tta ggt tgg gaa ttt gga       48
Ala Lys Glu Ala Ser Ser Tyr Asp Tyr Ile Leu Gly Trp Glu Phe Gly
1               5                   10                  15 gga ggc gtt cca gaa cac aaa aaa gaa gaa aat                           81
Gly Gly Val Pro Glu His Lys Lys Glu Glu Asn
            20                  25
```

<210> SEQ ID NO 6
<211> LENGTH: 27
<212> TYPE: PRT
<213> ORGANISM: Plasmodium falciparum

<400> SEQUENCE: 6

Ala Lys Glu Ala Ser Ser Tyr Asp Tyr Ile Leu Gly Trp Glu Phe Gly
1               5                   10                  15

Gly Gly Val Pro Glu His Lys Lys Glu Glu Asn
            20                  25

<210> SEQ ID NO 7
<211> LENGTH: 84
<212> TYPE: DNA
<213> ORGANISM: Plasmodium falciparum
<220> FEATURE:
<221> NAME/KEY: CDS
<222> LOCATION: (1)..(84)
<223> OTHER INFORMATION: MSP3c coding sequence

<400> SEQUENCE: 7 cca gaa cac aaa aaa gaa gaa aat atg tta tca cat tta tat gtt tct      48
Pro Glu His Lys Lys Glu Glu Asn Met Leu Ser His Leu Tyr Val Ser
1               5                   10                  15 tca aag gat aag gaa aat ata tct aag gaa aat gat                      84
Ser Lys Asp Lys Glu Asn Ile Ser Lys Glu Asn Asp
            20                  25

<210> SEQ ID NO 8
<211> LENGTH: 28
<212> TYPE: PRT
<213> ORGANISM: Plasmodium falciparum

<400> SEQUENCE: 8

Pro Glu His Lys Lys Glu Glu Asn Met Leu Ser His Leu Tyr Val Ser
1               5                   10                  15

Ser Lys Asp Lys Glu Asn Ile Ser Lys Glu Asn Asp
            20                  25

<210> SEQ ID NO 9
<211> LENGTH: 123
<212> TYPE: DNA
<213> ORGANISM: Plasmodium falciparum
<220> FEATURE:
<221> NAME/KEY: CDS
<222> LOCATION: (1)..(123)
<223> OTHER INFORMATION: MSP3d coding sequence

<400> SEQUENCE: 9 atg tta tca cat tta tat gtt tct tca aag gat aag gaa aat ata tct      48
Met Leu Ser His Leu Tyr Val Ser Ser Lys Asp Lys Glu Asn Ile Ser
1               5                   10                  15 aag gaa aat gat gat gta tta gat gag aag gaa gaa gag gca gaa gaa      96
Lys Glu Asn Asp Asp Val Leu Asp Glu Lys Glu Glu Ala Glu Glu
            20                  25                  30 aca gaa gaa gaa gaa ctt gaa gaa aaa                                 123
Thr Glu Glu Glu Glu Leu Glu Glu Lys
            35                  40

<210> SEQ ID NO 10
<211> LENGTH: 41
<212> TYPE: PRT
<213> ORGANISM: Plasmodium falciparum

<400> SEQUENCE: 10

```
Met Leu Ser His Leu Tyr Val Ser Ser Lys Asp Lys Glu Asn Ile Ser
1               5                   10                  15

Lys Glu Asn Asp Asp Val Leu Asp Glu Lys Glu Glu Glu Ala Glu Glu
                20                  25                  30

Thr Glu Glu Glu Glu Leu Glu Glu Lys
        35                  40
```

```
<210> SEQ ID NO 11
<211> LENGTH: 99
<212> TYPE: DNA
<213> ORGANISM: Plasmodium falciparum
<220> FEATURE:
<221> NAME/KEY: CDS
<222> LOCATION: (1)..(99)
<223> OTHER INFORMATION: MSP3e coding sequence

<400> SEQUENCE: 11 gaa gaa aat gac aaa aaa aaa gaa caa gaa aaa gaa caa agt aat gaa      48
Glu Glu Asn Asp Lys Lys Lys Glu Gln Glu Lys Glu Gln Ser Asn Glu
1               5                   10                  15 aat aat gat caa aaa aaa gat atg gaa gca cag aat tta att tct aaa      96
Asn Asn Asp Gln Lys Lys Asp Met Glu Ala Gln Asn Leu Ile Ser Lys
                20                  25                  30 aac                                                                   99
Asn
```

```
<210> SEQ ID NO 12
<211> LENGTH: 33
<212> TYPE: PRT
<213> ORGANISM: Plasmodium falciparum

<400> SEQUENCE: 12

Glu Glu Asn Asp Lys Lys Lys Glu Gln Glu Lys Glu Gln Ser Asn Glu
1               5                   10                  15

Asn Asn Asp Gln Lys Lys Asp Met Glu Ala Gln Asn Leu Ile Ser Lys
                20                  25                  30

Asn
```

```
<210> SEQ ID NO 13
<211> LENGTH: 159
<212> TYPE: DNA
<213> ORGANISM: Plasmodium falciparum
<220> FEATURE:
<221> NAME/KEY: CDS
<222> LOCATION: (1)..(159)
<223> OTHER INFORMATION: MSP3f coding sequence

<400> SEQUENCE: 13 aat tta att tct aaa aac cag aat aat aat gag aaa aac gta aaa gaa      48
Asn Leu Ile Ser Lys Asn Gln Asn Asn Asn Glu Lys Asn Val Lys Glu
1               5                   10                  15 gct gct gaa agc atc atg aaa act tta gct ggt tta atc aag gga aat      96
Ala Ala Glu Ser Ile Met Lys Thr Leu Ala Gly Leu Ile Lys Gly Asn
                20                  25                  30 aat caa ata gat tct acc tta aaa gat tta gta gaa gaa tta tcc aaa     144
Asn Gln Ile Asp Ser Thr Leu Lys Asp Leu Val Glu Glu Leu Ser Lys
        35                  40                  45 tat ttt aaa aat cat                                                 159
Tyr Phe Lys Asn His
    50
```

```
<210> SEQ ID NO 14
```

```
<211> LENGTH: 53
<212> TYPE: PRT
<213> ORGANISM: Plasmodium falciparum

<400> SEQUENCE: 14

Asn Leu Ile Ser Lys Asn Gln Asn Asn Asn Glu Lys Asn Val Lys Glu
1               5                   10                  15

Ala Ala Glu Ser Ile Met Lys Thr Leu Ala Gly Leu Ile Lys Gly Asn
            20                  25                  30

Asn Gln Ile Asp Ser Thr Leu Lys Asp Leu Val Glu Glu Leu Ser Lys
        35                  40                  45

Tyr Phe Lys Asn His
    50
```

IDENTIFICATION OF A CONSERVED REGION OF *PLASMODIUM FALCIPARUM* MSP3 TARGETED BY BIOLOGICALLY ACTIVE ANTIBODIES

CROSS REFERENCE TO RELATED APPLICATIONS

This application claims the benefit under 35 U.S.C. 119(e) of U.S. Provisional Application No. 60/598,062, filed Aug. 3, 2004, which is hereby incorporated by reference.

REFERENCE TO SEQUENCE LISTING

This application contains a Sequence Listing describing nucleic acid and polypeptide sequences of the invention.

BACKGROUND OF THE INVENTION

1. Field of the Invention

*Plasmodium falciparum* Merozoite Surface Protein 3 (MSP3) C-terminal polypeptides, including immunogenic and antigenic peptides which contain B cell epitopes and T helper epitopes and which inhibit the growth of *Plasmodium falciparum*.

2. Description of Related Art

The asexual blood-stage multiplication of the malarial parasite is responsible for the acute symptoms of malaria in humans. Epidemiological observations have shown that adults living in endemic areas, although they are constantly reinfected and frequently carry parasites, control their levels of parasitemia and show substantial clinical resistance, compared with children [1].

Repeated infections and continued exposure to the malarial parasite are required to reach this level of immunity against disease [2]. This state of naturally acquired immunity against disease, a phenomenon that is called premonition [3], is not a sterile immunity and is marked by chronic lowgrade parasitemia without clinical symptoms.

The passive transfer of serum IgG from clinically immune individuals has been shown to be able to control disease and the level of parasitemia in nonprotected individuals who are exposed to geographically diverse parasite strains [4-6].

The present inventors previously showed that the protection afforded by IgG has no major direct effect on parasite invasion and growth in red blood cells (RBCs)—rather, it acts in association with blood monocytes through an antibody-dependent cellular inhibition (ADCI) mechanism that inhibits parasite development [7].

The cytophilic nature of protective IgG has been established [8, 9], and the importance of these antibodies in protection against malaria has also been demonstrated in other independent studies [10, 11].

The inventors' search for the targets of the protective antibodies, using ADCI (antibody-dependent cellular inhibition) as a functional assay, led them to identify merozoite surface protein 3 (MSP3) as one such target [12]. MSP3 is associated with merozoite surface molecules, possibly through the coiled-coil structures that have been predicted to be formed by the heptad repeats and the C-terminal leucine zipper domain [13]. The N-terminal part of the molecule consists of regions that are polymorphic among different strains.

In contrast, the C-terminal part of the molecule is highly conserved among the various isolates of the parasite [14, 15], and it is this region that was earlier identified by screening of a *Plasmodium falciparum* expression library by use of functional ADCI assays [12]. However, previous studies of MSP3 have focused only on a 27-aa region (aa 184-210, corresponding to the 3D7 strain, MSP3b) of the C-terminal part, which was earlier identified as a target of protective antibody response in hyperimmune serum samples [12].

BRIEF DESCRIPTION OF THE INVENTION

One aspect of the invention was the further identification and characterization of the antigenicity or immunogenicity of segments of the C-terminal part of the MSP3 molecule. Six overlapping peptides were designed (MSP3a, MSP3b, MSP3c, MSP3d, MSP3e, and MSP3f), each of which represented a different region of the conserved C-terminal part of the molecule. They were used to analyze the naturally occurring immune responses in individuals from the malaria-endemic village of Dielmo, Senegal, and evaluate their role in providing protection against malaria. The functional role of human antibodies specific to each region was assessed under in vitro conditions in the ADCI assay and was further confirmed by passive transfer in vivo in an immunodeficient mouse model grafted with *P. falciparum*-infected human RBCs [16, 17].

Using these methods, the present inventors discovered a 68-aa region of MSP3 (amino acid residues 184-251) which is a target for naturally occurring protective antibody responses. This region defines the minimal domain essential for the design of any vaccine construct based on MSP3. Other antigenically and immunogenically important segments of the MSP3 molecule were also identified.

Targets. An important aspect of the invention is the use of these newly identified MSP3 segments as immunogenic targets for detecting or inducing immune responses to *Plasmodium falciparum*, including humoral and cellular responses.

Peptide-based vaccines. The MSP3 peptides of the present invention may be administered as peptides, as peptide multimers, for example, repeats of at least 2, 5, 10, 20 or 50 units of the same peptide epitope or MSP3 segment, peptide conjugates, or as a portion of a multideterminant hybrid or chimeric protein molecule. These products may be combined with a suitable adjuvant, carrier or excipient which are known in the art and which are also incorporated by reference to *Current Protocols in Molecular Biology*, vol. 2, chapter 11 (1987-2005), see e.g. sections 11.12 and 11.16.

Passive immunization. Passive immunization of individuals with one or more antibodies, including polyclonal, monospecific, or monoclonal antibodies, produced to immunogenic MSP3 determinants, or antibodies isolated using these determinants, is also contemplated.

Nucleic-acid based vaccines. Polynucleotides encoding these MSP3 segments may be used in nucleic-acid based vaccines, including in vectors and host cells which express epitopes of the MSP3 polypeptide.

Peptide-based detection methods. The MSP3 segments discovered by the inventors can also be used in assays to identify serum samples containing antibodies to *Plasmodium falciparum* or to evaluate the immunological status of a naïve, infected or previously-infected individual. Peptide-based detection methods, such as ELISA, are well-known in the art and are incorporated by reference to Chapter 10 of *Current Protocols in Molecular Biology*, vol. 2 (1987-2005).

Nucleic acid-based detection methods. The nucleic acids encoding these determinants (or the complementary sequences) may also be used to identify the presence of *Plasmodium falciparum* nucleic acids using PCR-based methods, as primers, or as probes, for example, as affixed to a solid substrate such as a DNA chip for hybridization with *Plasmodium* nucleic acid samples. Methods such as PCR are well-known in the art and are incorporated by reference to Chapter 15 of *Current Protocols in Molecular Biology*, vol. 2 (1987-2005).

Recombinant polypeptide expression. Such nucleic acids may, of course, be used to recombinantly produce MSP3 peptides or polypeptides or fused with other *Plasmodium* epitopes or immunogenic determinants to produce chimeric or hybrid polypeptides containing the MSP3 determinants of the present invention. Vectors, host cells and expression methods for recombinant expression of proteins are well-known in the art and generally involve inserting a DNA sequence encoding a peptide or polypeptide into a vector, transforming a host cell with the vector and expressing the recombinant protein in the transformed host cells. Recombinant expression of proteins is well known in the art, as are suitable vectors and host cells for expressing proteins, such as MSP3. Such methods, vectors and host cells are incorporated by reference to Chapter 1, 2, 3 and 9 of *Current Protocols in Molecular Biology*, vol. 1 (1987-2005) and Chapter 16 "Protein Expression" in vol. 3. Fusion proteins comprising the *Plasmodium* peptide determinants of the present invention may be produced by conventional fusion protein methods, including those incorporated by reference to Chapter 16 of *Current Protocols in Molecular Biology*, vol. 3 (1987-2005). Expression is not limited to prokaryotic cells such as *E. coli*, but may also include yeast, mammalian, insect cells or plant cells. Methods for purifying such proteins are well-known and are incorporated by reference to Chapter 10 of *Current Protocols in Molecular Biology*, vol. 2 (1987-2005).

BRIEF DESCRIPTION OF THE DRAWINGS

FIG. 6 depicts MSP3 protein amino acid sequence and shows the location of the MSP3a, MSP3b, MSP3c, MSP3d, MSP3e and MSP3f peptides. This figure also compares the amino acid sequences of MSP3a, MSP3b, and MSP3c of the present invention and with the MSP3a, MSP3b, and MSP3c shown by Oeuvray et al., Blood 84: 1594-1602, (1994), see FIG. 7 of Oeuvray et al. NP 700818 corresponds to SEQ ID NO: 3. MSP3a corresponds to residues 167-191 of SEQ ID NO: 3. The Oeuvray sequence below MSP3a also corresponds to residues 167-191 of SEQ ID NO: 3, but contains H at position 167 and R at position 169. MSP3b and the Oeuvray sequence depicted under it correspond to residues 184-210 of SEQ ID NO: 3. MSP3c and the Oeuvray sequence depicted under it correspond to residues 203-230 of SEQ ID NO: 3, except that the lower Oeuvray sequence has a substitution of E at position 230. MSP3d, 3e and 3f respectively correspond to residues 211-251, 275-307, and 302-354 of SEQ ID NO: 3. The Overlapping peptide at the bottom of FIG. 6, MSP3b+MSP3c+MSP 3d, corresponds to residues 184-251 of SEQ ID NO: 3.

The patent or application file contains at least one drawing (FIG. 6) executed in color. Copies of this patent or patent application publication with color drawing(s) will be provided by the office upon request and payment of the necessary fee.

DETAILED DESCRIPTION OF THE PREFERRED EMBODIMENTS

In the search for candidates for a malaria vaccine, the inventors focused studies on antigens targeted by the most potent immunity—that acquired over the years by individuals living in hyperendemic areas. The inventors have found that this premunition is mediated by IgG that is active through an indirect mechanism, which implicates monocytes when the inventors used ADCI to identify MSP3 as a target of protective IgG [12].

Figure 1:
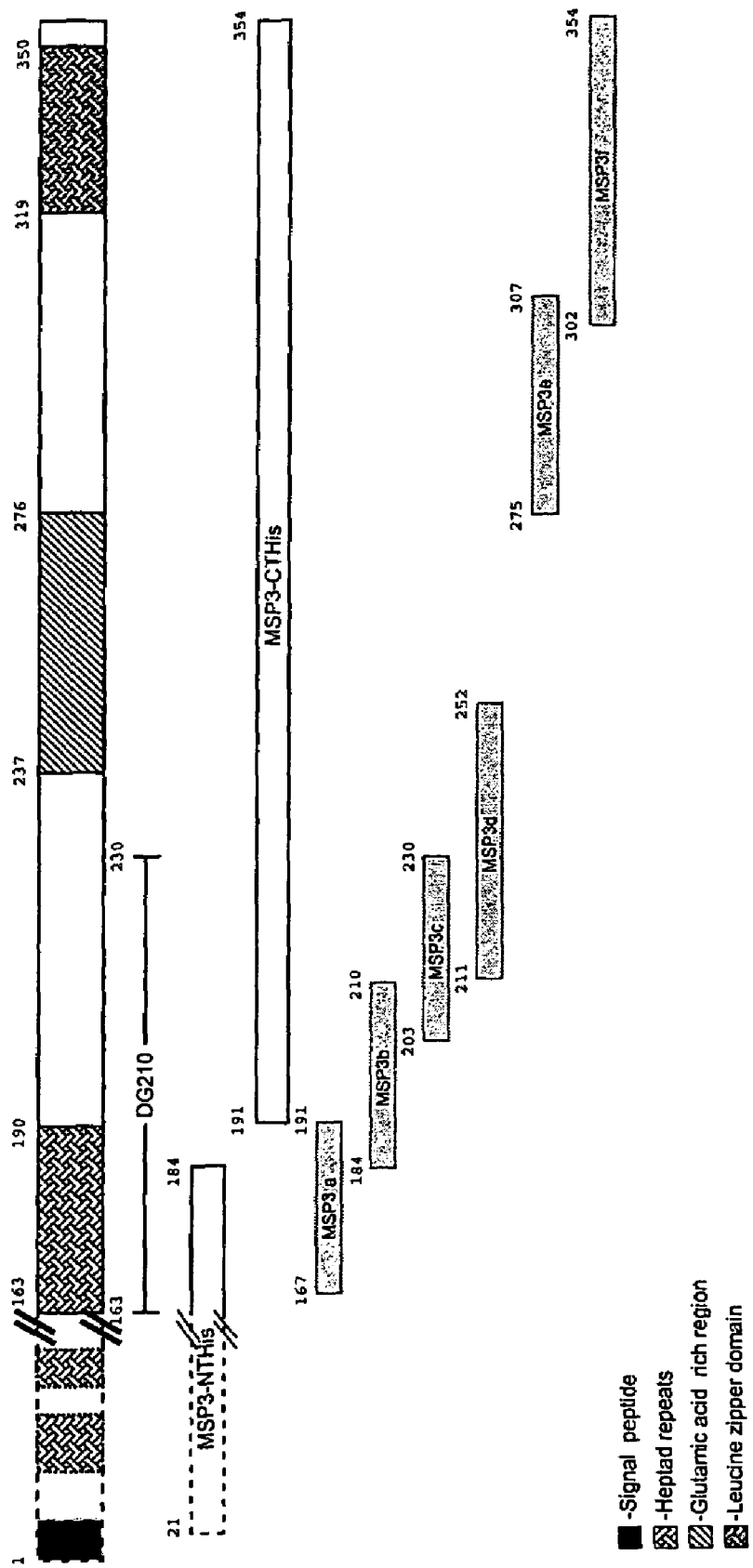
FIG. 1. Schematic presentation of *Plasmodium falciparum* merozoite surface protein 3 (MSP3) and the design of MSP3 recombinant proteins (MSP3-NTHis and MSP3-CTHis) and peptides (MSP3a, MSP3b, MSP3c, MSP3d, MSP3e, and MSP3f). The representation of the N-terminal part of MSP3 is compressed here (dotted line). DG210 represents the lgt11 expression clone originally identified as the target of protective antibodies [8]. The numbers show amino-acid positions for each region on the basis of the sequence derived from the 3D7 strain.

One objective of the present inventors was to characterize the antigenic and immunogenic determinants within the conserved C terminus of MSP3 and to evaluate the function and biological effects of the corresponding antibodies. Indeed, the C-terminal half of the molecule, starting from the third heptad repeat, is highly conserved in the different isolates tested so far [14, 15], whereas the N-terminal half of MSP3 shows an overall dimorphism (3D7-like and K1-like) [14, 15]. Therefore, it was decided to focus on the C-terminal region, because part of it (DG210; FIG. 1) was identified to be a target of protective human antibodies in an initial study by the inventors [12] and because antigen conservation is a critical criterion for the successful development of a malaria vaccine. Using six overlapping synthetic peptides covering the conserved C-terminal half of MSP3, it was shown that antibody patterns to each region differ markedly in terms of prevalence, titer, isotype distribution, association with clinical protection, and antiparasitic activity in vitro and in vivo. Antibody titers against MSP3a and MSP3e were lower than those of the remaining 4 peptides. Responses to MSP3b, MSP3c, MSP3d, and MSP3f were mostly of cytophilic IgG subclasses—predominantly of IgG1 isotype against MSP3f and IgG3 isotype against the others. A similar difference in subclass response to distinct regions of a single protein has been reported for MSP1 [26]. These observations suggest that IgG class switching involved during the maturation of the antibody response toward different regions of the MSP3 C terminal is regulated independently. The factors that regulate the maturation of antibodies are not well understood but would be influenced by the nature of the antigen in conjunction with contact-dependent signals from T cells, particularly the cytokines they secrete [27]. Recent observations, however, have suggested that the nature of the malaria antigen might be the major factor that determines antibody subclass [28], which seems to be the case in the inventors' study. The availability of very detailed clinical information, which is a major characteristic of the setup in the village of Dielmo, Senegal, led us to address subclass patterns in relation to protection against the occurrence of malaria. Taking into account the confounding effect of age, it was observed that IgG3 responses to MSP3b, MSP3c, and MSP3d were significantly associated with protection. These results are in agreement with those of independent studies that involved larger sample sizes [29] (C. Oeuray, C. R., J. L. Pé rignon C. Muller-Graf, A. Tall, C. Rogier, J. F. Trape, and P. D., unpublished data), which have shown an association between the IgG3 response against MSP3b and protection from malaria. For other merozoite surface vaccine candidates, a skewing toward the IgG3 antibody response has been reported for MSP2 in various ethnic groups and under different conditions of malaria transmission [30, 31]; this could be correlated with clinical immunity to malaria [32]. Similarly, the antibody response to the polymorphic block 2 region of MSP1, which has been identified as a target of immunity to clinical malaria, is also skewed toward the IgG3 subclass [33]. However, at least in the latter case, the mechanism of action of these antibodies remains elusive, because it is generally assumed that biologically active anti-MSP1 antibodies are directed to the C-terminal part of the antigen [34].

In contrast, in the present study, the use of functional in vitro ADCI assays provided information about the antiparasitic, biological activity of antibodies toward various regions. Because they were performed under conditions that allowed comparisons, they demonstrated critical differences in antibodies that target different regions of MSP3. It is of interest that very different approaches led to similar conclusions— that is, the in vitro ADCI assays pointed to the importance of exactly the same peptides (MSP3b, MSP3c, and MSP3d) as those indicated by the immunoepidemiological studies. The reasons for this lack of effect of antibodies to MSP3a and MSP3f remains to be investigated. In the case of MSP3f, it is possible that antibodies might not access this epitope on the merozoite surface, because the leucine-zipper domain forms coiled-coil interactions with other molecules [13, 14]. The reliability of in vitro findings could also be confirmed under in vivo conditions [16]. On passive transfer in P. falciparum-infected mice grafted with human monocytes and with long-lasting stable parasitemia, anti-MSP3b and MSP3d antibodies were found to be effective in reducing the P. falciparum parasite load.

The vaccine potential of MSP3 was recently confirmed by the protection elicited against P. falciparum challenge in Aotus nancymai monkeys immunized with full-length MSP3 in Freund's adjuvant [35]. This observation is in agreement with the inventors own epidemiological and biological findings. However, the present study has provided additional information derived from the analysis of human immune responses for the design of future vaccine constructs. Indeed, the N terminal of MSP3, although able to induce antibody with functional activity in ADCI, is of debatable value, because of its polymorphism. Furthermore, its inclusion could divert the immune response away from the important conserved region. Within the C-terminal part, the region MSP3e-f was also found to be less valuable, because of the low prevalence and low levels of antibody response to MSP3e and anti-MSP3f antibodies devoid of biological effect. Each of the 3 peptides (MSP3a, MSP3b, and MSP3c) investigated proved to define a non-cross-reactive T cell epitope for populations in endemic areas. Recent vaccine trials performed using the construct defined in the present study confirmed this finding and designated the peptide MSP3d as an additional T cell-epitopic region (R. Audran, M. Cachat, F. Lurati, S. Soe, O. Leroy, G. C., P. D., and F. Spertini, unpublished data). In summary, the results of immunoepidemiological studies and functional assays led us to define a region of the MSP3 molecule consisting of the sequences of MSP3b-MSP3d. It was found that antibodies with antiparasitic effect develop against this region, which covers MSP3b-MSP3d, in humans who have been naturally exposed to malaria. This information is of practical value for future clinical trials for the rational design of subunit vaccine constructs derived from MSP3.

The term MSP3 refers to the MSP3 sequence as found in Plasmodium falciparum. SEQ ID NO: 1 shows the nucleic acid sequence encoding MSP3 from Plasmodium falciparum strain 3D7 and SEQ ID NO: 2 depicts the corresponding MSP3 amino acid sequence. MSP3 recombinant protein constructs and peptides may be designed based the P. falciparum 3D7 strain sequence (NCBI protein_id, NP_700818.1) (SEQ ID NO: 2).

Fragments of MSP3, especially fragments of the C-terminal of MSP3 which are less immunologically variable than N-terminal fragments, may be isolated or produced by conventional means. Six fragments of MSP3, which correspond to the conserved region of MSP3 C-terminal region are described by SEQ ID NOS: 4, 6, 8, 10, 12 and 14. Nucleic acid sequences which encode these peptides are depicted by SEQ ID NOS: 3, 5, 7, 9, 11 and 13.

| Fragment | MSP3 residues | |
|---|---|---|
| MSP3a | 167-191 | (SEQ ID NO: 4) |
| MSP3b | 184-210 | (SEQ ID NO: 6) |
| MSP3c | 203-230 | (SEQ ID NO: 8) |
| MSP3d | 211-251 | (SEQ ID NO: 10) |
| MSP3e | 275-307 | (SEQ ID NO: 12) |
| MSP3f | 302-354 | (SEQ ID NO: 14). |

To increase the antigenic specificity of MSP3 C-terminal fragments they may be selected to omit the MSP3 sequence between amino acid residues 253-274, which contain a high number (72%) glutamic acid ("E") residues. Glutamate-rich antigenic determinants may exhibit cross-reactivity among several different P. falciparum antigens [19]. These peptides may be synthesized according to standard peptide synthesis procedures [20]. Peptides comprising these peptides or immunogenic or antigenic determinants of these peptides may also be produced as described by *Current Protocols In Molecular Biology*, vol. 2, chapter 11, sections 11.15-11.16 (1987-2005).

A peptide epitope or antigenic determinant of the present invention may comprise at least 5-50 amino acid residues, e.g., 5, 6, 7, 8, 9, 10, 11, 12, 15, 20, 25, 30, 35, 50 or more amino acid contiguous residues, depending on the nature of the epitope, for example, on whether the epitope is a B cell epitope or a T cell epitope. Conformational or discontinous epitopes comprising different segments or residues of the peptides identified by, for example, by comparison of antibody binding to MSP3 antigen and to substitutional variants of the MSP3 antigen produced by substitution of at least 1, 2, 3, 4 or 5 amino acids of a MSP3 C-terminal peptide. Similar substitutional analysis may be used to identify sequential epitopes.

Haptenic determinants of the peptides of the invention may contain fewer than 6-20 amino acid residues or lack residues recognized by T cells or lack the ability to bind to particular MHC Class I or II molecules, and be immunogenic when combined with an appropriate carrier moiety.

Modified forms of MSP3 may be produced by conventional mutagenesis and selection methods so long as they have at least 90, 95 or 99% sequence similarity with SEQ ID NO: 2. Such similarity may be determined by an algorithm, such as those described by *Current Protocols in Molecular Biology*, vol. 4, chapter 19 (1987-2005) or by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482-489 (1981), to find the best segment of identity or similarity between two sequences. Gap performs global alignments: all of one sequence with all of another similar sequence using the method of Needleman and Wunsch, J. Mol. Biol. 48:443-453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

Similarly, fragments of MSP3, such as the 68 amino acid fragment (amino acid residues 184-251 of MSP3) described above, may be further modified so long as they retain at least 90, 95 or 99% similarity with the corresponding fragment of SEQ ID NO: 2, 4, 6, 8, 10, 12 or 14. Such modified peptides should also retain at least one functional property of the corresponding unmodified polypeptide, such as the ability to bind to an antibody that binds to SEQ ID NO: 2, especially protective antibodies, or to induce antibodies or T cell responses to SEQ ID NO: 2. Methods for synthesizing or recombinantly producing mutant or variant peptides are well-known in the art and are also incorporated by reference to are incorporated by reference to Chapter 8 of *Current Protocols in Molecular Biology*, vol. 1 (1987-2005). The peptides comprising segments of the C-terminal residues of MSP3 may also be modified by substitution of 1, 2, 3, 4 or 5 or more amino acids to increase their immunogenicity or antigenicity or their ability to be restricted by particular MHC Class I or II molecules, for example, by modification of the residues (agretope) involved in binding to a particular type of MHC molecule.

Modified forms of MSP3 or its fragments may be encoded by polynucleotides which hybridize under stringent conditions (e.g., comprising washing at 50-68° C. in 0.1×SSC) to the complements of the polynucleotides of SEQ ID NOS: 1, 3, 5, 7, 9, 11, or 13 or to the complements of polynucleotides encoding the polypeptides of SEQ ID NOS: 2, 4, 6, 8, 10, 12, or 14. Such hybridization conditions may comprise hybridization at 5×SSC at a temperature of about 50 to 68° C. Washing may be performed using 2×SSC and optionally followed by washing using 0.5×SSC. For even higher stringency, the hybridization temperature may be raised to 68° C. or washing may be performed at 50 to 68° C. in a salt solution of 0.1×SSC. Other conventional high-stringency hybridization procedures and conditions may also be used as described by *Current Protocols in Molecular Biology*, (1987-2005), see e.g. Chapter 2.

MSP3 products, such as peptides, modified peptides, peptide conjugates, etc. may be screened for functional immunological properties using antibodies that recognize epitopes of MSP3 or by their ability to induce (or block induction) of humoral or cellular responses specific to MSP3. Growth inhibitory antibodies effective by cooperating with blood monocytes in ADCI (antibody-dependent cellular inhibition of parasite growth) mechanisms may be employed. ADCI is beneficially employed for identifying cytophilic antibody subclasses IgG1 and IgG3, and for targeting B cell epitopes contained in MSP3 peptides MSP3b (SEQ ID NO: 6), MSP3c (SEQ ID NO: 8) and MSP3d (SEQ ID NO: 10).

Polynucleotide sequences encoding the MSP3 of strain 3D7 are known (ID Number NC_004314). Polynucleotide sequences encoding modified MSP3 polypeptides or particular subfragments of MSP3 may be isolated or synthesized by conventional means. Antisense nucleic acids may also be produced by conventional methods based on the corresponding sequences encoding MSP3 or regulating its expression.

Polynucleotide sequences encoding immunogenic fragments of MSP3 can be used to produce immunogenic constructs, such as hybrid or chimeric polypeptides or immunoconjugates, that induce protective immune responses against *Plasmodium falciparum*. Immunoconjugates may also be produced by aggregation, or by chemical linking of subfragments of MSP3 to known immunogenic carriers, such as KLH.

MSP3 peptide or nucleic acid products may be admixed with one or more adjuvants, such as aluminum hydroxide, complete Freund's Adjuvant ("CFA") or Incomplete Freunds Adjuvant ("IFA"), ISCOMS, lipoproteins, liposomes, and Ribi adjuvant, depot adjuvants, as well as other adjuvants which are known in the art and are incorporated by reference to Paul, *Fundamental Immunology*, Chapter 37 (1993).

Other vaccination strategies which employ the MSP3 C-terminal epitopes of the invention may also be used such as immunization with synthetic peptides in Freunds Adjuvant, lipopeptides, recombinant yeast Ty particles, intramuscular administration of naked DNA encoding these C-terminal peptide epitopes, or intravenous injection of dendritic cells charged with peptides. These methods are described by Charneau et al., U.S. Pat. No. 6,682,907 which is hereby incorporated by reference.

Nucleic acid based vaccines comprising polynucleotides which encode MSP3 C-terminal immunogenic or antigenic determinants may also be produced using polynucleotides encoding the polypeptides of SEQ ID NOS: 2, 4, 6, 8, 10, 12, and 14. Such a vaccine may make use of triplex structure DNA as disclosed by Charneau et al., U.S. Pat. No. 6,682,907, which is hereby incorporated by reference.

Passive immunization may be conducted by administering to a subject polyclonal, monospecific or monoclonal antibodies that recognize antigenic determinants in the MSP3 C-terminal peptides of the invention. Passive immunization procedures are well known in the art and are also incorporated by reference to Cryz et al., ed., Vaccines and Immunotherapy, New York Pergammon Press (1991): 1-463. Passive immunization is preferably performed using antibodies from the same species as the recipient, e.g., affinity purified human antibodies or humanized antibodies for human subjects. It may also involve selection and administration of one or more particular Ig types or subclasses. Procedures for producing humanized antibodies are well-known in the art.

EXAMPLES

Antigens. MSP3 recombinant protein constructs and peptides were designed on the basis of the *P. falciparum* 3D7 strain sequence (NCBI protein_id, NP_700818.1). Two recombinant hexahistidine-tagged proteins, MSP3-NTHis$_{21-184}$ and MSP3-CTHis$_{191-354}$, were purified as described by Theisen, et al., Clin. Diagn. Lab. Immunol. 1995; 2:30-4. Six overlapping peptides were designed (MSP3a$_{167-191}$, MSP3b$_{184-210}$, MSP3c$_{203-230}$, MSP3d$_{211-252}$, MSP3e$_{275-307}$, and MSP3f$_{302-354}$), each of which represented a different region of the conserved C-terminal part of the molecule. A small region (aa 253-274; 72% glutamic acid) was excluded from this analysis because glutamate-rich antigenic determinants exhibit crossreactivity among several different *Plasmodium falciparum* antigens [19]. Peptides were synthesized by conventional means [20].

Human serum and lymphocyte samples. For the affinity purification of antibodies specific to each MSP3 region, serum samples were used from thirty hyperimmune individuals from Ivory Coast that had been previously used for passive-transfer experiments in Thai patients with malaria and were found to be effective in controlling disease and parasitemia [6].

For immunoepidemiological studies, plasma samples were used from 48 permanent residents of the village of Dielmo, Senegal, who had various degrees of exposure to malaria (age, 3.5-53.4 years; mean age, years; mean stay in the 13.1±1.8 village, 707/730 days of follow-up). In this region, malaria transmission is intense and perennial (~200 infected mosquito bites/person/year); over the course of two-year period, the mean number of malaria attacks was 2.4±5.4 episodes/person. Nineteen individuals had no malaria attack (mean age, 15.7±3.1 years), whereas twenty nine individuals had at least 1 malaria attack (mean age, years) during the next 2 years. All inhabitants of Dielmo were actively monitored by medical doctors on a daily basis for febrile episodes, and those due to malaria were accurately diagnosed as described elsewhere [21]. This allowed us to examine the pattern of the IgG isotype response toward different regions of MSP3 in individuals who were clearly distinguishable as "protected" (no malaria attack) or "nonprotected" ($\geq 1$ malaria attack) during the 2-year follow-up period of the study. This group was representative of the whole village in terms of age distribution, with respect to occurrence or absence of malaria attack. Mononuclear cells obtained from inhabitants of Dielmo were transported within 4 h to laboratories in Dakar and used for T cell proliferation and the determination of interferon (IFN)-γ against MSP3a, MSP3b, and MSP3c peptides, according to methods described elsewhere [22, 23]. In brief, the proliferative responses of the cells were assessed in quadruplicate in 96-well round-bottomed plates (Nunclon; Nunc) by incubation for 6 days at 37° C. in 5% $CO_2$ in the presence of each peptide used at 10 mg/mL, followed by the addition of 1 mCi of [3H]thymidine overnight and counting of the incorporated radioactivity in a liquid scintillation counter. Unstimulated cultures served as negative controls, and purified protein derivative and phytohemagglutinin were used as positive controls.

The IFNγ concentration in pooled supernatants from quadruplicate wells was assessed by a capture ELISA performed in duplicate, by use of the anti-human IFN-γ monoclonal antibody (MAb) 350B10G6 and biotin-labeled MAb 67F12A8 (Biosource) for coating and revealing, respectively, according to the manufacturer's instructions. The reaction was revealed by use of streptavidin-horseradish peroxidase and tetra-methyl benzidine chromogen, and the optical density was measured at 450 nm. For practical reasons, mainly the number of cells available per donor, the other 3 peptides used for antibody assays could not be included in T cell assays. Lymphoproliferation studies were performed with samples from 61 inhabitants (29 female and 32 male; mean age, 27.31 years), and IFN-g secretion was studied in 31 inhabitants (19 female and 12 male; mean age, 33.94 years).

The 3 peptides proved to induce no significant response in peripheral blood mononuclear cells from 16 control, non-malaria-exposed donors (data not shown), which indicated that they had no mitogenic or superantigenic effect. ELISA. The ELISA was performed for the detection of total IgG and subclasses, as described elsewhere [8, 9]. Monoclonal mouse anti-human subclasses IgG1-IgG4 (clones NL16 [Boehringer], HP6002 [Sigma], Zg4 [Immunotech], and RJ4 [Immunotech]) were selected for their affinity and reactivity for African allotypes and were used as secondary antibodies at dilutions of 1:2000, 1:5000, 1:5000, and 1:1000, respectively.

The specific reactivity of each serum sample was obtained by subtracting the optical density value of a control protein (0.25 mg of bovine serum albumin/well) from that of the test antigens. For calculating the threshold of significance of antibody responses, a set of eight randomly selected serum samples from individuals never exposed to malaria was tested against each antigen, as controls. Results were expressed as the ratio of the mean optical density from test serum samples to the mean optical density of control subset +3x the SD of the control serum samples. Serum samples were considered to be positive for ratios $\geq 1$.

Affinity purification of antibodies. Because the ADCI assay requires the cooperation of antibodies with the Fc-γ RII receptor [7], a group of thirty hyperimmune serum samples from individuals from Ivory Coast were first screened for IgG subclass distribution against different MSP3 peptides and recombinants. Serum samples were selected for the affinity purification of antibodies against any given MSP3 construct on the basis of their high reactivity against that region, with minimal reactivity toward the adjacent peptides and a high content of cytophilic IgG antibodies (IgG1 and IgG3). Independent serum pools (each of which was made up of 5-7 individual serum samples) were used to affinity purify antibodies to different regions of MSP3. The ratios of cytophilic to noncytophilic IgG subclasses (IgG1+IgG3:IgG2+IgG4) of the serum pools used were estimated to be 9.56 for MSP3NT, 4.25 for MSP3CT, 1.29 for MSP3a, 3.86 for MSP3b, 1.29 for MSP3c, 4.58 for MSP3d, 1.59 for MSP3e, and 3.68 for MSP3f. Previous studies have shown that the profile of cytophilic antibodies observed in affinity-purified antibodies was similar to that of the serum sample pool used for affinity purification.

Affinity purification was done as described by [24], by use of a 2.5% aqueous suspension of polystyrene beads (mean diameter, 10 mm; Polysciences) to coat the peptides or recombinant proteins. Specific antibodies were eluted by use of 0.2 mol glycine/L (pH 2.5) and were immediately neutralized to pH 7.0 by use of a 2 mol/L aqueous Tris solution. Affinity purified antibodies were dialyzed extensively against PBS followed by RPMI and were concentrated by use of Centricon concentrators (Millipore), filter sterilized, and, after the addition of 1% albumax (Gibco BRL), stored at 4_C. Affinity purified antibodies were used at a concentration of 10 mg/mL in ELISA to ascertain their specificity. Immunofluorescence assay (IFA). Because the ability of the antibodies to recognize the native parasite protein is the critical factor in biological assays, IFA was used to adjust the concentration of affinity-purified antibodies. IFA was performed on air-dried, acetone-fixed, thin smears of *P. falciparum* mature schizonts, as described elsewhere [25], to assess the binding activity of affinity-purified antibodies to the parasite protein. The effective concentration of each antibody was adjusted to a 1:200 IFA end-point titer for use in functional assays.

Functional in vitro antibody assays. The antibody dependent, monocyte-mediated ADCI assays were performed in duplicate by use of laboratory-maintained strains 3D7 and Uganda Palo-Alto, as described elsewhere [7]. Monocytes from healthy, non-malaria-exposed donors were prepared as described elsewhere [7]. The affinity-purified antibodies, adjusted to a concentration yielding a 1/200 IFA end-point titer, were added at a rate of 10 mL in 90 mL of complete culture medium, which yielded a final titer of 1/20 in the ADCI assay. After cultivation for 96 h, the level of parasitemia was determined on Giemsa-stained thin smears from each well by the microscopic examination of ≧50,000 erythrocytes. Monocyte-dependent parasite inhibition is expressed as the specific growth inhibition index (SGI):

SGI=1−([percentage of parasitemia with monocytes and test IgG/percentage of parasitemia with test IgG)/(percentage of parasitemia with monocytes and normal IgG/percentage of parasitemia with normal IgG])×100.

Although the SGI calculation takes into account a possible direct antiparasite effect of monocytes, because this is observed with 10%-15% of monocyte preparations, they were excluded as an additional precaution.

Passive immunization of *P. falciparum*-infected immunocompromised mice. The use of the *P. falciparum*-human RBC (HuRBC)-Beige-Xid-Nude (BXN) mouse model for assessing the effect of antibodies on different blood-stage antigens of *P. falciparum* has been detailed elsewhere [16]. In brief, 6-8-week old male BXN mice (Charles River Laboratories), manipulated under pathogen-free conditions, were treated with liposomes that contained dichloromethylenediphosphonate (Roche Diagnostics) and antipolymorphonuclear neutrophil MAbNIMP-R14 (NIMR), to reduce their innate immune response. *P. falciparum*-infected human RBCs were injected intraperitoneally (i.p.) on day 0, and uninfected RBCs were injected at 4-day intervals. The level of blood parasitemia was examined microscopically. Mice with stable parasitemia (0.1%-1%) were injected i.p. with human peripheral blood monocytes positively selected by CD14+ magnetic beads (MACS; Miltenyi Biotech), followed 24 h later by the injection of monocytes together with 200 mL of 6 3_10 affinity-purified antibodies to MSP3 at a 1:200 IFA end-point titer, as described above. Nonspecific esterase staining [7] showed that 198% of CD14+ cells were monocytes.

Statistical analysis. Univariate analysis was performed by use of the Mann-Whitney U test. Fisher's exact test was used for the contingency analysis. The association between the risk of malaria attack and the level of antibodies was tested with JMP software (SAS Institute), by use of a stepwise regression model in which the confounding effect of age was controlled. The analysis of variance was applied to the regression model. The test of the null hypothesis was based on the variance ratio denoted by F, and departures from the null hypothesis tended to give values of F that were greater than unity.

Figure 2:
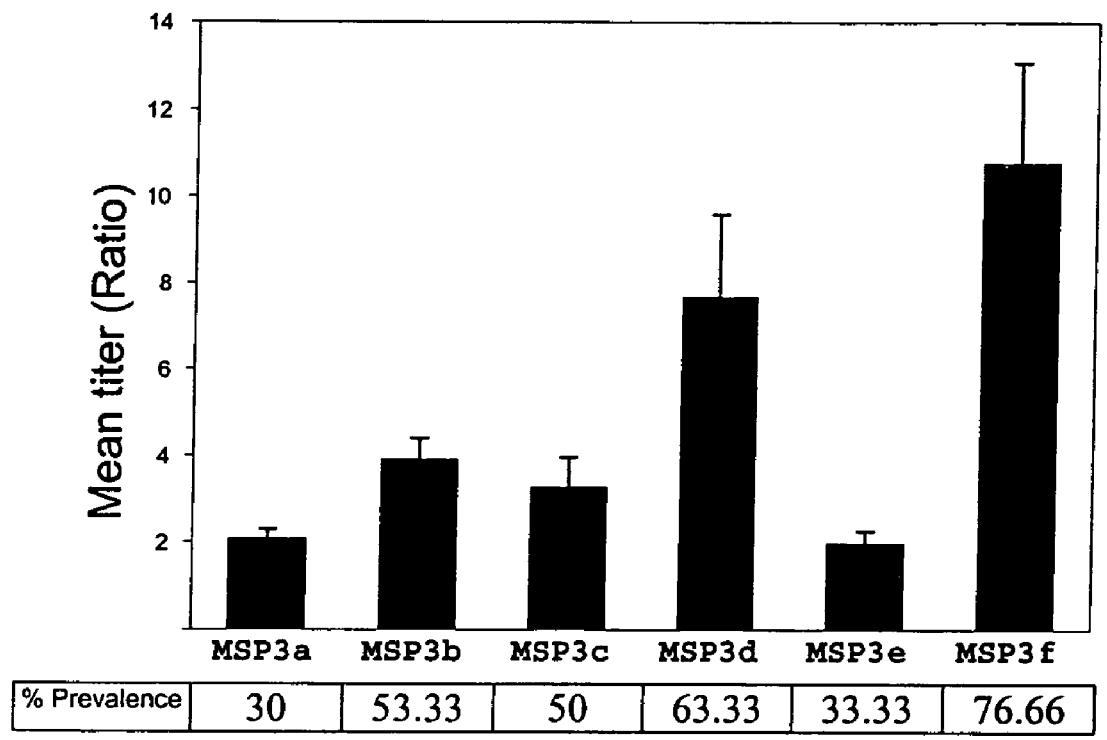
FIG. 2. Total IgG response against different regions of merozoite surface protein 3 (MSP3) in hyperimmune serum samples (n=30) from individuals from Ivory Coast, used to prepare protective IgG for passive-transfer experiments in humans [6]. Antibody reactivity was considered to be positive if the ratio of the mean optical density of the test serum samples to the mean optical density of control serum samples +3 times the SD of the control serum sample was ≧1. The figure represents the mean antibody titer (expressed as ratio) of positive serum samples against each region. The table shows the percentage prevalence of positive serum samples reactive to different regions of MSP3, in terms of total IgG.

Non-cross-reactive B cell epitopes defined by each of the six MSP3 C-terminal peptides. IgG responses were measured against different regions of the MSP3 C terminal (FIG. 1) in a group of 30 hyperimmune serum samples from individuals from Ivory Coast. As shown in FIG. 2, there were differences in the levels and prevalence of IgG toward each region, but antibody responses were detected against each of the C-terminal peptides. Antibodies were then affinity purified from selected hyperimmune serum samples specific to each peptide and examined for their reactivity against the other peptides. In this way, it was possible to affinity purify antibodies that were specific to each peptide but did not show cross-reactivity with other regions (see Table 1).

Table 1

Specificity of affinity-purified human anti-merozoite surface protein 3 (MSP3) antibodies, as determined by ELISA.

| Antibody | MSP3a | MSP3b | MSP3c | MSP3d | MSP3e | MSP3f |
|---|---|---|---|---|---|---|
| Anti-MSP3a | 0.78 | 0.09 | 0.08 | 0.08 | 0.09 | 0.08 |
| Anti-MSP3b | 0.05 | 1.11 | 0.09 | 0.08 | 0.09 | 0.07 |
| Anti-MSP3c | 0.07 | 0.10 | 1.04 | 0.09 | 0.09 | 0.08 |
| Anti-MSP3d | 0.10 | 0.08 | 0.16 | 1.01 | 0.09 | 0.09 |
| Anti-MSP3e | 0.08 | 0.08 | 0.08 | 0.08 | 0.95 | 0.10 |
| Anti-MSP3f | 0.07 | 0.07 | 0.08 | 0.08 | 0.10 | 0.92 |

NOTE.
Mean optical density values at 450 nm from duplicate wells are shown. All the peptides were used under identical coating conditions. Bold type represents positive reactivity.

These observations indicated that each of the peptides covering the MSP3 C-terminal defines at least one B cell epitope that does not share antigenic determinants with other regions. Each of the affinity-purified antibodies was also found to be positive in IFAs of *P. falciparum* asexual blood stages, which indicates that antipeptide antibodies were reactive with the native parasite protein.

Distinct isotype patterns of the IgG response toward different MSP3 peptides. Plasma from 48 individuals, 3-53 years old, from the endemic village of Dielmo, Senegal, was analyzed to study the distribution and pattern of IgG isotype response against the different regions of the C-terminal part of MSP3 defined by the peptides.

Figure 3:
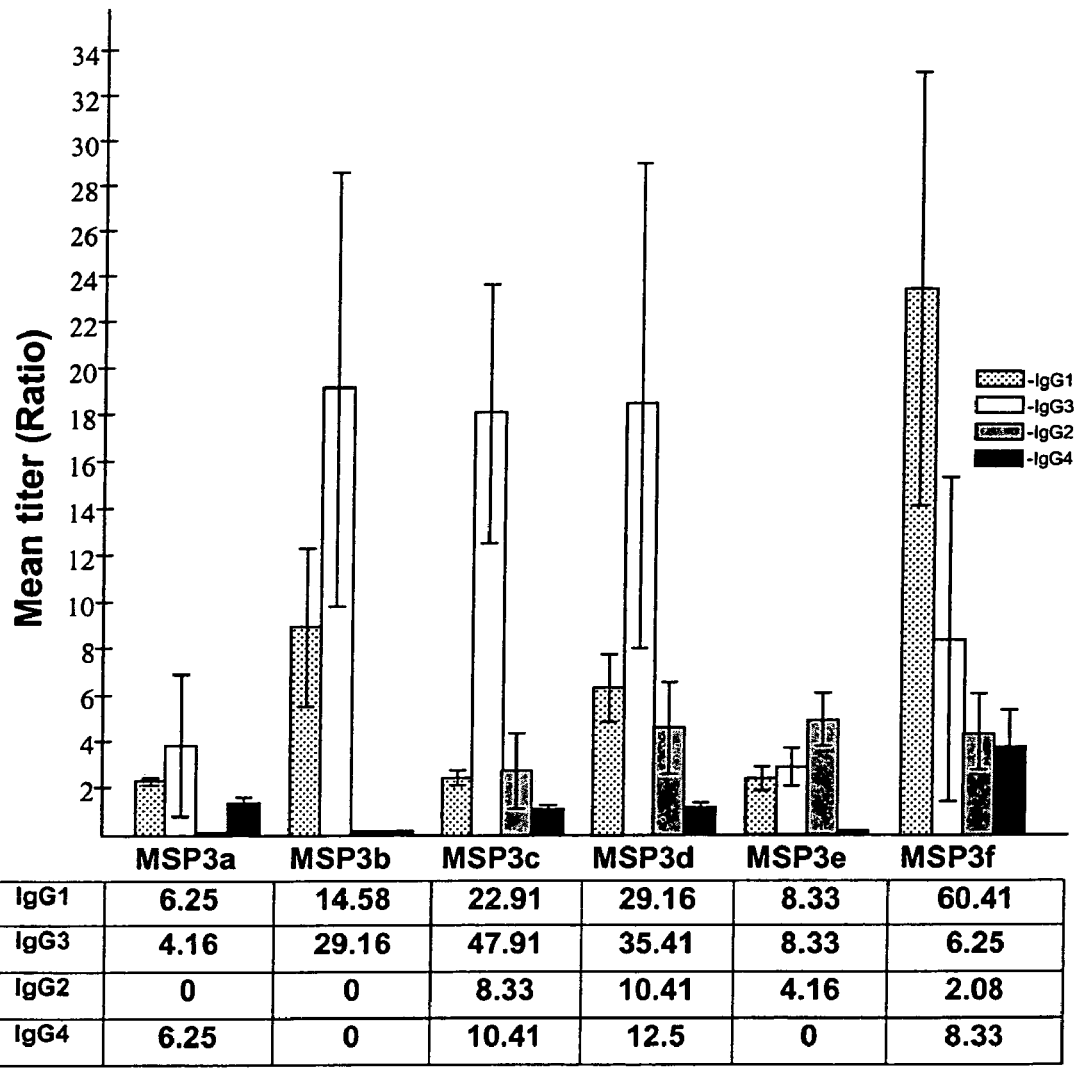
FIG. 3. Prevalence and mean titer of antibodies against different regions of merozoite surface protein 3 (MSP3) in serum samples (n=48) from Dielmo, Senegal. Antibody reactivity was considered to be positive if the ratio of the mean optical density of test serum samples to the mean optical density of control serum samples +3 times the SD of the control serum samples was ≧1. The figure represents antibody titers (expressed as a ratio) of the positive serum samples against each region. The table shows the percentage prevalence of positive serum samples reactive to different regions of MSP3, in terms of IgG isotype.

As shown in FIG. 3, both the level of antibody response and the pattern of IgG isotype were distinct against each region. The prevalence of responders varied for each region of MSP3 (6.25%-60.41% for IgG1, 4.16%-7.91% for IgG3, 0%-10.41% for IgG2, and 0%-12.5% for IgG4). It was found that antibodies to MSP3a and MSP3e were less prevalent, and, when they were present, they were detected only at low levels. Antibodies to MSP3b, MSP3c, MSP3d, and MSP3f were the most prevalent and were predominantly of cytophilic subclasses.

Among the cytophilic isotypes, IgG3 reactivity was found to be predominant against MSP3b, MSP3c, and MSP3d. By contrast, IgG1 reactivity against MSP3f was stronger and more prevalent than that against IgG3. This suggests that the antibody response elicited to any region of MSP3 was not dependent on a response to other regions. It had been observed earlier that the cytophilic IgG response plays an important role in protection against malaria [8-11]. The inventors further addressed the relationship between clinical protection that had been monitored on a daily basis and the pattern of isotype responses observed against each peptide. Protection was defined as the absence of any clinical malaria attack during the 2 years after plasma samples were obtained. Higher IgG3 titers against MSP3b, MSP3c, and MSP3d were observed among protected subjects as compared to nonprotected subjects.

An association between the levels of IgG3 antibodies directed to MSP3b and MSP3d and protection from occurrence of malaria attack (P=0.037 and 0.057, respectively) was observed. In the case of MSP3c, this association did not reach statistical significance; however, levels of anti-MSP3c IgG3 antibodies were twice as high in individuals who did not develop malaria, compared with those who did. The association between levels of IgG1 and protection against malaria attack was observed to be significant for MSP3d (P=0.025), and a similar trend was observed for MSP3b (P=0.328), but not for MSP3c. Neither IgG1 nor IgG3 responses to MSP3f were found to be associated with protection. IgG2 and IgG4 antibody responses against different regions of MSP3 were detected only at low levels and were not found to be associated with protection. In a further step, a multivariate stepwise regression analysis was performed to control for age, by use of dichotomous variables of both antibody response (responders or nonresponders) and occurrence of malaria attack (protected or nonprotected). A significant association of protection with IgG3 antipeptide responses was observed against 3 of 6 peptides—MSP3b (F=4.98, P=0.025), MSP3c (F=3.02, P=0.082), and MSP3d (F=6.57, P=0.01)—but not against the other 3.

Inhibition of parasite growth by naturally occurring antibodies against MSP3b, MSP3c, and MSP3d in functional in vitro ADCI assays. To assess the function of naturally occurring human antibodies to different regions of MSP3 in ADCI assays, each affinity-purified antibody was adjusted to a concentration that yielded the same reactivity to the native parasite protein.

Results (FIG. 4) showed that the level of parasite inhibition elicited by antibodies against the recombinant proteins MSP3NT and MSP3CT were comparable to that observed for the pool of African IgG (PIAG), which was used elsewhere for a passive-transfer experiment in humans [6].

Figure 4:
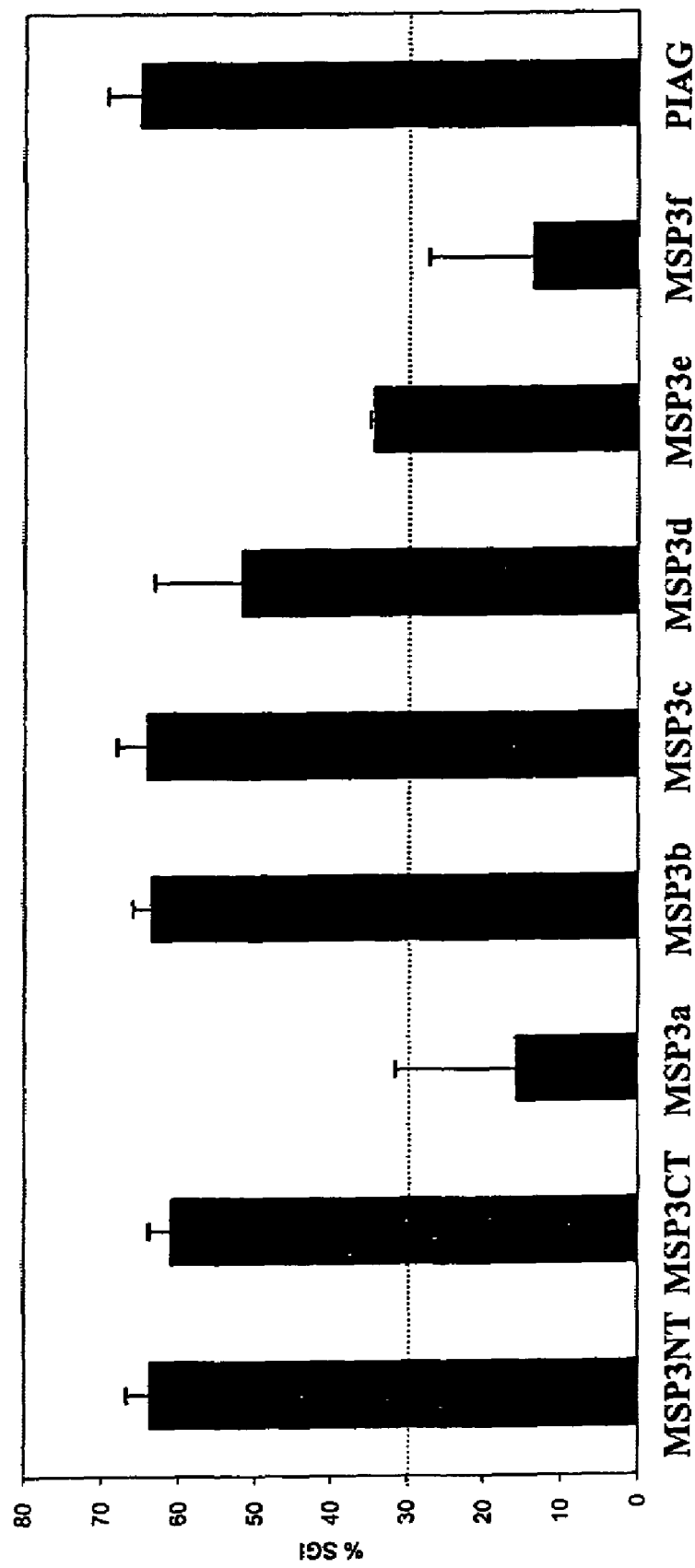
FIG. 4. Effect of affinity-purified human antibodies on parasite growth in antibody-dependent cellular inhibition assay. The histograms represent mean values of the percentage of the specific growth inhibition index (SGI; as explained in the text) from 2 independent experiments ±SE; values 130% are significant. PIAG, positive control IgG from the pool of serum samples from adults from Ivory Coast used for passive-transfer experiments in humans [6].

Anti-MSP3b, -MSP3c, and -MSP3d affinity-purified antibodies were found to exert a strong monocyte mediated antiparasitic activity in ADCI that was comparable to that of antibodies against MSP3CT and PIAG, whereas anti-MSP3a and -MSP3f antibodies were not found to have parasite inhibitory activity (FIG. 4). Anti-MSP3e antibodies showed only marginal antiparasite activity that was slightly higher than the threshold level of significance. Results were reproducible among 4 independent ADCI assays. At the concentrations used, none of the above-mentioned antibodies showed the direct inhibition of parasite growth.

Strong reduction of P. falciparum parasitemia by anti-MSP3b and anti-MSP3d antibodies in a humanized mouse model. The observation from the in vitro ADCI assays that anti-MSP3b, -MSP3c, and -MSP3d antibodies were strongly effective at inhibiting parasite growth was further assessed in vivo by use of the P. falciparum-HuRBC-BXN mouse model. The value of this new mouse model for studying the in vivo effect of human antibodies and antimalarial drugs on the blood-stage growth of P. falciparum has been recently documented [16, 17]. The inventors chose to study antibodies to MSP3d and MSP3f, which were positive and negative in ADCI, respectively, compared with anti-MSP3b antibodies, which were used as positive controls, whose antiparasitic effect has already been demonstrated [16].

Figure 5:
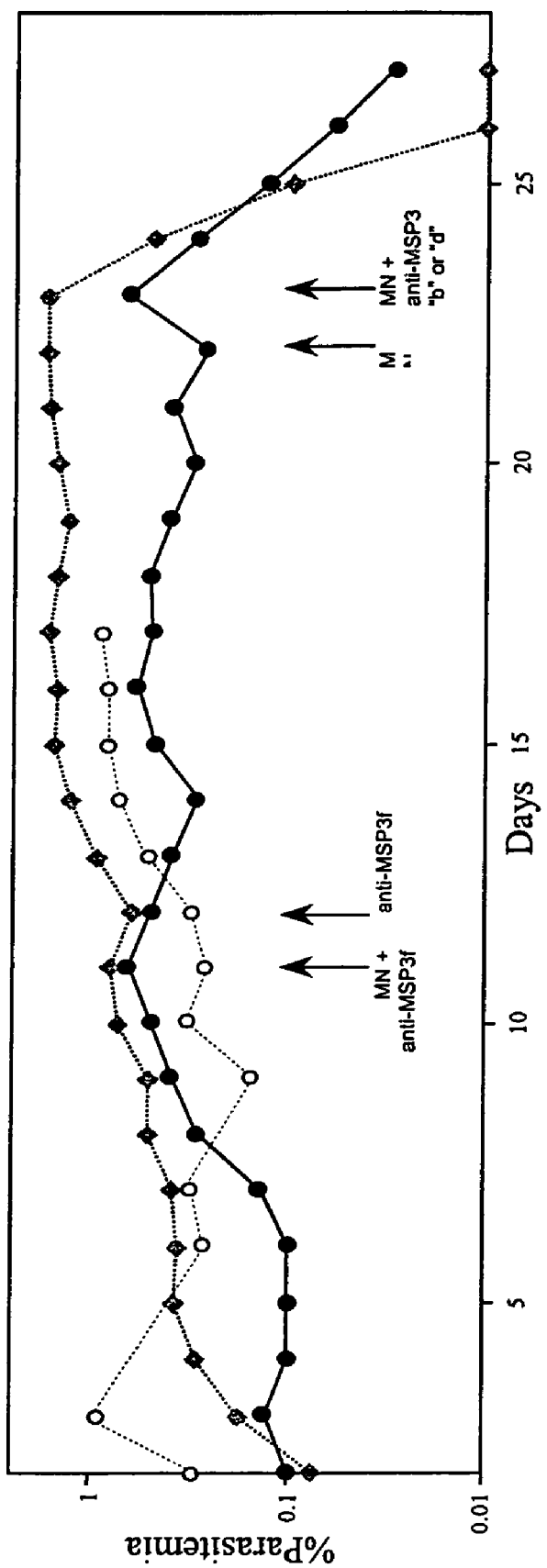
FIG. 5. In vivo transfer of affinity-purified human anti-merozoite surface protein 3 (MSP3) antibodies, together with human peripheral blood monocytes in *P. falciparum*—human red blood cell—Beige-Xid-Nude mice. The curves show the course of parasitemia as determined by microscopic examination of thin blood smears from mice injected with anti-MSP3b antibodies (gray diamonds), anti-MSP3d antibodies (black circles), or control anti-MSP3f antibodies that were ineffective in the antibody-dependent cellular inhibition assay (white circles). Arrows, days at which injections were made, first of human monocytes (MNs) and then followed by monocytes together with anti-MSP3 antibodies (200 mL; immunofluorescence assay titer, 1:200).

As seen in FIG. 5, the level of parasitemia increased and reached a plateau over the next 3 weeks. The injection of anti-MSP3f antibodies with human monocytes did not affect parasite growth, in agreement with the results of the in vitro ADCI assays. In the other 2 mice, the injection of human monocytes alone on day 22 did not affect parasite growth, in keeping with earlier observations [16].

The injection of affinity-purified anti-MSP3b or -MSP3d human antibodies on day 23 resulted in a sharp decrease in parasitemia. The passive transfer of anti-MSP3b antibodies resulted in the clearance of parasites. The passive transfer of anti-MSP3d antibodies resulted in a decrease of parasitemia >95% (FIG. 5). Thus, results from the in vivo passive transfer in this mouse model confirmed in vitro results and further validated the functional antiparasite activity of naturally occurring antibodies against the 68-aa region covered by peptides MSP3b and MSP3d.

T cell responses against MSP3 peptides in malaria-exposed individuals. T lymphocyte responses could be studied against only 3 (MSP3a, MSP3b, and MSP3c) of 6 C-terminal peptides in inhabitants from Dielmo, Senegal, because of practical limitations in field. The proliferative response, which was determined by use of peripheral blood lymphocytes from 61 individuals (age range, 1-84 years; mean age, 27.34 years) showed that the prevalence of T helper cell responders was 16.4% against MSP3a, 28% against MSP3b, and 21.3% against MSP3c, respectively. IFN-g secretion, which was monitored in 31 of these individuals, showed that the prevalence of IFN-g responders was 42% against MSP3a, 55% against MSP3b, and 61.3% against MSP3c. These results indicate that each of the three MSP3 peptides tested defines at least 1 T cell epitope. In addition, IFN-g secretion results suggested that at least some of the responding cells belonged to the Th1-like type.

REFERENCES

1. Baird J K, Jones T R, Danudirgo E W, et al. Age-dependent acquired protection against *Plasmodium falciparum* in people having two years exposure to hyperendemic malaria. Am J Trop Med Hyg 1991; 45:65-76.
2. McGregor I A, Wilson R J M. Specific immunity: acquired in man. In: Wernsdorfer W H, McGregor I A, eds. Malaria: principles and practice of malariology. London: Churchill Livingstone, 1989:559-619.
3. Sergent E, Parrot L. L'immunité, la pré munition et la ré sistance inné e. Arch Inst Pasteur Alger 1935; 23:279-319.
4. Cohen S, McGregor I A, Carrington S. Gamma globulin and acquired immunity to human malaria. Nature 1961; 192:733-7.
5. Edozien J C, Gilles H M, Udeozo I O. Adult and cord-blood gamma globulin and immunity to malaria in Nigerians. Lancet 1962; 2:951-5.
6. Sabchareon A, Burnouf T, Ouattara D, et al. Parasitologic and clinical human response to immunoglobulin administration in *falciparum* malaria. Am J Trop Med Hyg 1991; 45:297-308.
7. Bouharoun-Tayoun H, Attanath P, Chongsuphajaisiddhi T, Druilhe P. Antibodies which protect man against *P. falciparum* blood stages do not on their own inhibit parasite growth and invasion in vitro but act in cooperation with monocytes. J Exp Med 1990; 172:1633-41.
8. Bouharoun-Tayoun H, Druilhe P. Evidence for an isotype imbalance, which may be responsible for the delayed acquisition of protective immunity. Infect Immun 1992; 60:1473-81.
9. Bouharoun-Tayoun H, Druilhe P. Antibodies in *falciparum* malaria: what matters most, quantity or quality? Mem Inst Oswaldo Cruz 1992; 87:229-34.
10. Oeuvray C, Theisen M, Rogier C, Trape J F, Jepsen S, Druilhe P. Cytophilic immunoglobulin responses to *Plasmodium falciparum* glutamate-rich protein are correlated with protection against clinical malaria in Dielmo, Senegal. Infect Immun 2000; 68:2617-20.
11. Groux H, Gysin J. Opsonization as an effector mechanism in human protection against asexual blood stages of *Plasmodium falciparum*: functional role of IgG subclasses. Res Immunol 1990; 141:529-42.
12. Oeuvray C, Bouharoun-Tayoun H, Gras-Masse H, et al. Merozoite surface protein-3: a malaria protein inducing antibodies that promote *Plasmodium falciparum* killing by co-operation with blood monocytes. Blood 1994; 84:1594-602.
13. Mills K E, Pearce J A, Crabb B S, Cowman A F. Truncation of merozoite surface protein-3 disrupts its trafficking and that of acidic-basic repeat protein to the surface of *P. falciparum* merozoites. Mol Microbiol 2002; 43:1401-11.
14. McColl D J, Anders R F. Conservation of structural motifs and antigenic diversity in the *Plasmodium falciparum* merozoite surface protein-3 (MSP3). Mol Biochem Parasitol 1997; 90:21-31.
15. Huber W, Felger I, Matile H, Lipps H J, Steiger S, Beck H. Limited sequence polymorphism in the *Plasmodium falciparum* merozoite surface protein 3. Mol Biochem Parasitol 1997; 87:231-4.
16. Badell E, Oeuvray C, Moreno A, et al, Human malaria in immunocompromised mice: an in vivo model to study defense mechanisms against *Plasmodium falciparum*. J Exp Med 2000; 192:1653-60.
17. Moreno A, Badell E, van Rooijen N, Druilhe P. Human malaria in immunocompromised mice: new in vivo model for chemotherapy studies. Antimicrob Agents Chemother 2001; 45:1847-53.
18. Theisen M, Vuust J, Gottschau A, Jespen S, Hogh B. Antigenicity and immunogenicity of recombinant glutamate-rich protein of *Plasmodium falciparum* expressed in *Escherichia coli*. Clin Diagn Lab Immunol 1995; 2:30-4.
19. Mattei D, Berzins K, Wahlgren M, et al, Cross-reactive antigenic determinants present on different *Plasmodium falciparum* blood-stage antigens. Parasite Immunol 1989; 11:15-29.
20. Roggero M A, Servis C, Corradin G. A simple and rapid procedure for the purification of synthetic polypeptides by a combination of affinity chromatography and methionine chemistry. FEBS Lett 1997; 408:285-8.
21. Trape J F, Rogier C, Konate L, et al. The Dielmo project: a longitudinal study of natural malaria infection and the mechanisms of protective immunity in a community living in a holoendemic area of Senegal. Am J Trop Med Hyg 1994; 51:123-37.
22. Behr C, Sarthou J L, Rogier C, et al. Antibodies and reactive T cells against the malaria heat-shock protein Pf72/Hsp70-1 and derived peptides in individuals continuously exposed to *Plasmodium falciparum*. J Immunol 1992; 149:3321-30.
23. Bottius E, BenMohamed L, Brahimi K, et al. A novel *Plasmodium falciparum* sporozoite and liver stage antigen (SALSA) defines major B, T helper, and CTL epitopes. J Immunol 1996; 156:2874-84.
24. Brahimi K, Perignon J L, Bossus M, Gras H, Tartar A, Druilhe P. Fast immunopurification of small amounts of specific antibodies on peptides bound to ELISA plates. J Immunol Methods 1993; 162:69-75.
25. Druilhe P, Khusmith S. Epidemiological correlation between levels of antibodies promoting merozoite phagocytosis of *Plasmodium falciparum* and malaria-immune status. Infect Immun 1987; 55:888-91.
26. Cavanagh D R, Dobano C, Elhassan I M, et al. Differential patterns of human immunoglobulin G subclass responses to distinct regions of a single protein, the merozoite surface protein 1 of *Plasmodium falciparum*. Infect Immun 2001; 69:1207-11.
27. Stavnezer J. Antibody class switching. Adv Immunol 1996; 61:79-146.
28. Garraud O, Perraut R, Diouf A, et al. Regulation of antigen-specific immunoglobulin G subclasses in response to conserved and polymorphic *Plasmodium falciparum* antigens in an in vitro model. Infect Immun 2002; 70:2820-7.
29. Soe S, Theisen M, Roussilhon C, Aye K S, Druilhe P. Association between protection against clinical malaria and antibodies to merozoite surface antigens in an area of hyperendemicity in Myanmar: complementarity between responses to merozoite surface protein 3 and the 220-kilodalton glutamate-rich protein. Infect Immun 2004; 72:247-52.
30. Taylor R R, Smith D B, Robinson V J, McBride J S, Riley E M. Human antibody response to *Plasmodium falciparum* merozoite surface protein 2 is serogroup specific and predominantly of the immunoglobulin G3 subclass. Infect Immun 1995; 63:4382-8.
31. Rzepczyk C M, Hale K, Woodroffe N, et al. Humoral immune responses of Solomon Islanders to the merozoite surface antigen 2 of *Plasmodium falciparum* show pronounced skewing towards antibodies of the immunoglobulin G3 subclass. Infect Immun 1997; 65:1098-100.
32. Taylor R R, Allen S J, Greenwood B M, Riley E M. IgG3 antibodies to *Plasmodium falciparum* merozoite surface protein 2 (MSP2): increasing prevalence with age and association with clinical immunity to malaria. Am J Trop Med Hyg 1998; 58:406-13.
33. Polley S D, Tetteh K K, Cavanagh D R, et al. Repeat sequences in block 2 of *Plasmodium falciparum* merozoite surface protein 1 are targets of antibodies associated with protection from malaria. Infect Immun 2003; 71:1833-42.
34. Egan A F, Burghaus P, Druilhe P, Holder A A, Riley E M. Human antibodies to the 19 kDa C-terminal fragment of *Plasmodium falciparum* merozoite surface protein 1 inhibit parasite growth in vitro. Parasite Immunol 1999; 21:133-9.
35. Hisaeda H, Saul A, Reece J J, et al. Merozoite surface protein-3 and protection against malaria in *Aotus nancymai* monkeys. J Infect Dis 2002; 185:657-64.

The invention claimed is:

1. An isolated or purified peptide consisting of at least 5 consecutive amino acid residues from residues 167-354 of SEQ ID NO: 2 (MSP3), wherein said peptide comprises at least one epitope, and
wherein said polypeptide is no longer than a polypeptide consisting of residues 167-354 of SEQ ID NO: 2 and does not contain any amino acid residues extraneous to residues 167-354 of SEQ ID NO: 2.

2. The peptide of claim 1, which consists of at least 5 consecutive amino acid residues between residues 211 and 354 of SEQ ID NO: 2.

3. The peptide of claim 1, which consists of at least 5 consecutive amino acid residues between residues 167-191 of SEQ ID NO: 2 (MSP3).

4. The peptide of claim 1, which consists of at least 5 consecutive amino acid residues between residues 184-210 of SEQ ID NO: 2 (MSP3).

5. The peptide of claim 1, which consists of at least 5 consecutive amino acid residues between residues 203-230 of SEQ ID NO: 2 (MSP3).

6. The peptide of claim 1, which consists of at least 5 consecutive amino acid residues between residues 211-251 of SEQ ID NO: 2 (MSP3).

7. The peptide of claim 1, which consists of at least 5 consecutive amino acid residues between residues 275-307 of SEQ ID NO: 2 (MSP3).

8. The peptide of claim 1, which consists of at least 5 consecutive amino acid residues between residues 302-354 of SEQ ID NO: 2 (MSP3).

9. The peptide of claim 1, which comprises at least one epitope to which a parasite inhibitory antibody binds.

10. The peptide of claim 1 which comprises at least one T epitope.

11. The peptide of claim 1 which comprises at least one Th1 epitope.

12. A hybrid protein comprising the peptide of claim 1 and an exogenous polypeptide sequence.

13. The hybrid protein of claim 12 which comprises an exogenous polypeptide sequence from at least one Plasmodium falciparum polypeptide other than MSP3.

14. The hybrid protein of claim 12, which comprises an exogenous polypeptide that enhances the immunogenicity of said peptide when administered to a mammal.

15. A protein conjugate comprising the peptide of claim 1 and at least one covalently-linked carrier.

16. The protein conjugate of claim 15, which comprises carrier that enhances the immunogenicity of said peptide when administered to a mammal.

17. A composition comprising the peptide of claim 1 and at least one non-covalently associated carrier or excipient.

18. The composition of claim 17, which comprises a carrier or excipient that enhances the immunogenicity of said peptide when administered to a mammal.

19. The composition of claim 17, wherein said carrier or excipient comprises at least one substance selected from the group consisting of an oily emulsion, saponin, inorganic substance, bacterial extract, aluminum hydroxide and squalene.

20. The composition of claim 17, wherein said carrier or excipient comprises at least one substance selected from the group consisting of unilamellar liposomes, multilamellar liposomes, saponin micelles, and solid microspheres.

21. The composition of claim 17, further comprising at least Plasmodium falciparum immunogen that is not a peptide consisting of at least 5 consecutive amino acid residues from residues 167-354 of SEQ ID NO: 2 (MSP3).

22. An isolated or purified polypeptide which is at least 95% identical to the purified peptide of claim 1 and which induces an immunogenic response to Plasmodium falciparum when introduced into an animal wherein said polypeptide has at least 20 amino acid residues.

23. An isolated or purified polypeptide,
which is encoded by a polynucleotide which hybridizes under stringent conditions to the full complement of a polynucleotide encoding the peptide of claim 1, and
which induces an immunogenic response to Plasmodium falciparum when introduced into an animal;
wherein stringent conditions comprise washing at 50-68° C. in 0.1×SSC.

24. A method of inducing an immune response against Plasmodium falciparum, comprising:
administering an amount of at least one peptide of claim 1 to a mammal effective to induce an immune response against Plasmodium falciparum.

25. The method of claim 24, wherein the mammal is a human.

26. The method of claim 24, wherein said immune response is sufficient to reduce the severity of disease caused by Plasmodium falciparum or sufficient to reduce the incidence of Plasmodium falciparum infection in an immunized mammal.

27. A method for detecting antibodies to Plasmodium falciparum comprising:

contacting a biological sample suspected of containing said antibodies with the peptide of claim 1 for a time and under conditions suitable for binding, and
determining binding,
wherein the occurrence or amount of binding is indicative of the presence of antibodies to *Plasmodium falciparum* in said biological sample.

28. The isolated or purified polypeptide of claim 1, which consists of the 68 amino acid segment covered by peptides Msp3b, Msp3c, and Msp3d (residues 184-251 of SEQ ID NO: 2), or a fragment thereof of at least five consecutive amino acid residues.

29. The isolated or purified polypeptide of claim 1, which consists of the segment covered by peptides Msp3a, Msp3b, and Msp3c (residues 167-230 of SEQ ID NO: 2, or a fragment thereof of at least five consecutive amino acid residues.

* * * * *